United States Patent
Schjölin et al.

(10) Patent No.: US 11,801,219 B2
(45) Date of Patent: Oct. 31, 2023

(54) POUCH PRODUCT SUITABLE FOR APPLICATION IN AN ORAL CAVITY

(71) Applicant: Evaggelos Schjölin, Tyresö (SE)

(72) Inventors: Evaggelos Schjölin, Tyresö (SE); Eric Beaussant Törne, Tyresö (SE)

( * ) Notice: Subject to any disclaimer, the term of this patent is extended or adjusted under 35 U.S.C. 154(b) by 248 days.

(21) Appl. No.: 17/283,002

(22) PCT Filed: Sep. 21, 2020

(86) PCT No.: PCT/EP2020/076333
§ 371 (c)(1),
(2) Date: Apr. 5, 2021

(87) PCT Pub. No.: WO2021/063727
PCT Pub. Date: Apr. 8, 2021

(65) Prior Publication Data
US 2021/0361561 A1   Nov. 25, 2021

(30) Foreign Application Priority Data

Oct. 4, 2019 (SE) .................................... 1951137-7
Oct. 4, 2019 (SE) .................................... 1951138-5

(51) Int. Cl.
| | | |
|---|---|---|
| A61K 31/465 | (2006.01) | |
| A61K 36/81 | (2006.01) | |
| A61K 47/02 | (2006.01) | |
| A61K 47/26 | (2006.01) | |
| A61K 47/36 | (2006.01) | |
| A61K 47/38 | (2006.01) | |
| A61K 47/46 | (2006.01) | |
| A61K 9/00 | (2006.01) | |
| A61K 9/70 | (2006.01) | |
| A61K 36/185 | (2006.01) | |

(52) U.S. Cl.
CPC .............. *A61K 9/009* (2013.01); *A61K 9/006* (2013.01); *A61K 31/465* (2013.01); *A61K 36/185* (2013.01); *A61K 47/38* (2013.01); *A61K 47/46* (2013.01)

(58) Field of Classification Search
USPC ........................................................ 424/400
See application file for complete search history.

(56) References Cited

U.S. PATENT DOCUMENTS

2019/0269865 A1   9/2019  Vu et al.

FOREIGN PATENT DOCUMENTS

| EP | 1998748 B1 | 1/2015 | |
|---|---|---|---|
| EP | 3491940 A1 | 6/2019 | |
| WO | 2004056363 A1 | 7/2004 | |
| WO | WO 2005/023227 A2 * | 3/2005 | ............... A61K 9/22 |
| WO | WO 2007/104573 A2 * | 9/2007 | ............... A61K 9/14 |
| WO | WO 2007/126361 * | 11/2007 | |
| WO | 2015117011 A1 | 8/2015 | |
| WO | 2016103163 A1 | 6/2016 | |
| WO | 2018233781 A1 | 12/2018 | |
| WO | 2018233782 A1 | 12/2018 | |
| WO | 2018233795 A1 | 12/2018 | |
| WO | WO 2018/233781 * | 12/2018 | ............... A61K 9/00 |
| WO | WO 2018/233795 * | 12/2018 | ............... A61K 9/16 |
| WO | 2019115778 A1 | 6/2019 | |

OTHER PUBLICATIONS

Mayo Clinic, Ulcerative colitis (https://www.mayoclinic.org/diseases-conditions/ulcerative-colitis/symptoms-causes/syc-20353326) (Year: 2022).*
J. Rettenmaier & Söhne, Dietary Fibers & Functional Additives Vitacel Potato Fiber p. 12 (Year: 2022).*
JRS Rettenmaier Heweten MCC, Datasheet (Year: 2022).*
Wikipedia Cellulose fiber (https://en.wikipedia.org/wiki/Cellulose_fiber) (Year: 2022).*
Crohn's Disease (https://www.mayoclinic.org/diseases-conditions/crohns-disease/symptoms-causes/syc-20353304) (Year: 2022).*
International Search Report and Written Opinion of the International Searching Authority Application No. PCT/EP2020/076333 dated Dec. 23, 2020 14 pages.
Office Action Issued in Swedish Patent Application No. 1951137-7 dated Mar. 10, 2020 Six pages including Swedish Search Report.
Office Action Issued in Swedish Patent Application No. 1951138-5 dated Mar. 9, 2020 Ten pages including Swedish Search Report.
Office Action Issued in Russian Patent Application No. Application No. 2021108128/04(017504) (English Translation) dated Dec. 28, 2021.

* cited by examiner

*Primary Examiner* — Jeffrey T. Palenik
*Assistant Examiner* — Karen A. Ketcham
(74) *Attorney, Agent, or Firm* — Welsh IP Law LLC

(57) ABSTRACT

A pouch product comprising a sealable pouch material comprising i) 0 to 10 wt % *Cannabis*, ii) 0 to 10 wt % nicotine, whereby nicotine is present in the form of iia) tobacco or iib) as nicotine pure and as nicotine salicylic acid salt at a ratio of pure to salt of 0.20-1:1, and up to of one or more 100 wt % of iii) a sweetener, iv) a pH regulator, and v) essential oil as taste agent. The filling material further comprises vi) up to 76 wt % of a filler consisting of vi-1) 42 to 60 wt % microcrystalline cellulose and vi-2) 11 to 22 wt % potato fibers, at a ratio of 2.0-5:1, and vii) 0.1 to 5 wt % of xanthan gum as a wetting agent, whereby the ratio between microcrystalline cellulose, potato fibers and xanthan gum is 1.0-5:1:0.001-0.4.

16 Claims, No Drawings

POUCH PRODUCT SUITABLE FOR APPLICATION IN AN ORAL CAVITY

TECHNICAL FIELD

The present invention relates to a pouch product suitable for application in an oral cavity of a human comprising a sealable pouch material.

BACKGROUND

Delivery of nicotine by smoking has many known health related problems. Delivery of nicotine by means chew tobacco or snuff may potentially cause health problems such as dental problems. Snuff may be provided in pouches or as a tobacco concentrate without a pouch.

Nicotine replacement therapy is a medically approved way to take nicotine by means other than tobacco. It is used to help with quitting smoking or stopping chewing tobacco. It increases the chance of quitting smoking by about 55%.

*Cannabis*, also known as marijuana, among other names, is a psychoactive drug from the *Cannabis* plant used for medical or recreational purposes. The main psychoactive part of *Cannabis* is tetrahydrocannabinol (THC), one of the 483 known compounds in the plant, including at least 113 other cannabinoids. *Cannabis* can be used by smoking, vaporizing, within food, or as an extract.

*Cannabis* has mental and physical effects, such as creating a "high" or "stoned" feeling, a general change in perception, heightened mood, and an increase in appetite. Onset of effects is felt within minutes when smoked, and about 30 to 60 minutes when cooked and eaten. *Cannabis* is mostly used for recreation or as a medicinal drug, although it may also be used for spiritual purposes. In 2013, between 128 and 232 million people used *Cannabis* (2.7% to 4.9% of the global population between the ages of 15 and 65). Medical use of *Cannabis*, requiring the approval of a physician, has been legalized in a greater number of countries.

Tetrahydrocannabinol (THC) is the principal psychoactive constituent of *Cannabis*. With chemical name (−)-trans-$\Delta^9$-tetrahydrocannabinol, or IUPAC name (6aR,10aR)-delta-9-Tetrahydrocannabinol; (−)-trans-$\Delta^9$-Tetrahydrocannabinol, CAS Number 1972-08-3. The term THC as used in this application also refers to isomers, such as stereoisomer, diastereomer or metabolites thereof.

Cannabidiol (CBD) is a phytocannabinoid discovered in 1940. It has a IUPAC name 2-[(1R,6R)-6-Isopropenyl-3-methylcyclohex-2-en-1-yl]-5-pentylbenzene-1,3-diol, CAS Number 13956-29-1. It is one of 113 identified cannabinoids in *Cannabis* plants and accounts for up to 40% of the plant's extract. In 2018, clinical research on cannabidiol included preliminary studies on anxiety, cognition, movement disorders and pain.

Cannabidiol can be taken into the body in multiple ways, including by inhalation of *Cannabis* smoke or vapor, as an aerosol spray into the cheek, and orally. It may be supplied as CBD oil containing only CBD as the active ingredient (not including tetrahydrocannabinol (THC) or terpenes), a full-plant CBD-dominant hemp extract oil, capsules, dried *Cannabis*, or as a prescription liquid solution. CBD does not have the same psychoactivity as THC, and may change the effects of THC on the body if both are present. As of 2018, the mechanism of action for its biological effects has not been fully established.

Cannabinol (CBN) is a mildly psychoactive cannabinoid found only in trace amounts in *Cannabis*, and is mostly found in aged *Cannabis*. The IUPAC name is 6,6,9-Trimethyl-3-pentyl-benzo[c]chromen-1-ol, CAS Number 521-35-7. Pharmacologically relevant quantities are formed as a metabolite of tetrahydrocannabinol (THC). CBN acts as a partial agonist at the CB1 receptors, but has a higher affinity to CB2 receptors. However, it has lower affinities relative to THC. Degraded or oxidized *Cannabis* products, such as low-quality baled *Cannabis* and traditionally produced hashish, are high in CBN.

Unlike other cannabinoids, CBN does not stem directly from cannabigerol (CBG) or cannabigerolic acid (CBGA), but rather is the degraded product of tetrahydrocannabinolic acid (THCA). If *Cannabis* is exposed to air or ultraviolet light (for example, in sunlight) for a prolonged period of time, THCA will convert to cannabinolic acid (CBNA). CBN is then formed by decarboxylation of CBNA.

Medical use of *Cannabis* has been increased in recent years, especially for use in treatment of pain. Mostly, only CBD is administered when *Cannabis* is used for pain treatment. However, in treatment of pain in cancer, multiple sclerosis and arthritis, and in treatment or prevention of disorders like anxiety, both CBD and THC may be used, even in combination with CBN.

As mentioned above, *Cannabis* may be administered in different manners. Administration of drops of oil in the mouth cavity is often used. One general problem with administration of *Cannabis* is dosing of a predetermined amount of *Cannabis*. Controlled release of *Cannabis* from a dosage form is another problem, especially for simple and cost-effective dosage forms.

For smokers and other nicotine addicts, it is often difficult to administer nicotine when invalidated or hospitalized. For such patients, it might be convenient to be able to continue administering nicotine and/or *Cannabis* to the patient in an acceptable manner, i.e. not by smoking.

Different nicotine comprising tablets and pouches have been developed. WO2018/233795 discloses a pouch comprising nicotine in an ion exchange resins. These types of products are complex and expensive to manufacture.

EP1998748 discloses a snuff composition comprising a nicotine-cellulose combination having a certain release profile.

WO2004/056363 discloses a nicotine containing chewing gum for fast release of nicotine. The gum may comprise fillers, which are listed in long lists of varying types. Microcrystalline cellulose is used in the examples.

EP3491940 discloses a method for making a tobacco comprising pouch. Although lists of different fibers are mentioned, only propylene glycol is used in the examples.

WO2019/115778 discloses a nicotine pouch comprising monoglyceride for fast release of nicotine. Glycerides are used as moist filling material, optionally together with microcrystalline cellulose. A variety of other fillers are listed.

WO2018/233781 discloses a *Cannabis* containing pouch constituted of fillers and humectants and the like. Lists of these ingredients are disclosed. In the examples, microcrystalline cellulose, polyvinylpyrrolidone, isomalt and mannitol are included.

One problem with existing nicotine and/or *Cannabis* replacement therapies is a slow wettability of the nicotine product. This results in an uncomfortable feel of the pouch in the mouth cavity. This may also result in a slow release of nicotine from the product. Palatability is important for people who want to replace normal tobacco snus for non-tobacco snus. The non-tobacco snus must feel in a similar manner during use.

A further problem with existing pouches is the monolithic appearance of the products after wetting. Many products get too wet, or get a gummy texture or get a hard, cement-like texture. These textures are very different from the texture of a tobacco-comprising snus pouch. This reduced palatability of the product and thus makes the product unattractive for the user.

Yet another problem regards the retention of water by the product. Most products become to dry or hard when exposed to in house humidity. It seems a challenge to develop a product that remains humid and grainy over time, without becoming hard or gummy-like.

Yet another problem with existing products is the presence of taste agents over a longer period of use. The taste agents are either released too quickly leaving a tasteless product left in the mouth cavity or the taste agents are not released in sufficient quantities.

Another problem with existing nicotine replacement therapies is the release rate of nicotine from the product. It seems difficult to develop a product, whereby the nicotine is initially released quickly to relieve the cravings for the addict and subsequently released slowly over a longer period of time of at least 30 minutes. The same can be said for existing *Cannabis* comprising products.

SUMMARY

It is an aim of the present invention to at least partly overcome the above-mentioned problems, and to provide an improved pouch product.

This aim is achieved by a product as defined in claim 1.

According to an aspect of the invention, there is provided a pouch product suitable for application in an oral cavity of a human comprising a sealable pouch material containing a filling material comprising or consisting of
  i) 0 to 10 wt % *Cannabis*,
  ii) 0 to 10 wt % nicotine, whereby nicotine is either
    iia) present in the form of tobacco or
    iib) present as nicotine pure and as nicotine salicylic acid salt at a ratio of pure to salt of 0.20-1:1, and
    up to 100 wt % of one or more iii) a sweetener, iv) a pH regulator, and optionally v) essential oil as taste agent,
  vi) up to 76 wt % of a filler consisting of
    vi-1) 42 to 60 wt % microcrystalline cellulose and
    vi-2) 11 to 22 wt % potato fibers,
    whereby a ratio between microcrystalline cellulose and potato fibers is 2.0-5:1, and
  vii) 0.1 to 5 wt % of xanthan gum as a wetting agent,
whereby a ratio between microcrystalline cellulose, potato fibers and xanthan gum is 1.0-5:1:0.001-0.4, wherein wt % are weight percentages of the total weight of the filling material.

The inventors have found that the use of potato fibers in combination with microcrystalline cellulose (MCC) as a filler provides several advantages. Although potato fibers are mentioned in the literature in lists of fillers that can be used in a pouch or snuff/snus, no enabling examples are present. Without wanting to be bound by any theory, the larger grains of the potato fibers combined in the right ratio with the smaller grains from the MCC seems to provide a three dimensional network that allows proper mixing with the other ingredients in such a manner that ingredients like taste agents and *Cannabis* and/or nicotine are released at a preferable rate. Taste agents are being released throughout the use of the pouch, while *Cannabis* and/or nicotine is initially quickly released and subsequently slowly released over a period of 30 minutes to 3 hours. Potato fibers seem to have the advantage of combining the positive properties of insoluble fiber with its innate starch in a perfect way.

The combination of potato fibers with microcrystalline also provides for a product having an improved palatability compared to known products. The product does not become gummy-like nor hard.

The inventors have furthermore found that the addition of xanthan gum to the combination of potato fibers with microcrystalline in the right ratios further improves the product. The three-dimensional network of potato fibers, microcrystalline and xanthan gum seems to further improve the preferred releases of taste agents and *Cannabis* and/or nicotine mentioned above. This specific combination together with the combination of nicotine base and nicotine salt at the defined ratio, provides for a nicotine release that resembles the nicotine release from tobacco snus, i.e. initially quick and subsequently slow release overtime.

This combination of potato fibers, microcrystalline and xanthan gum at the defined ratios especially improves the wettability of the product. Throughout the use of the product, the product is not too wet, nor hard nor gummy-like. The feel of the product is comparable to the feel of tobacco snus. This improved palatability improves compliance of the user.

Another advantage of the combination of potato fibers, microcrystalline and xanthan gum at the defined ratios is related to humidity of the product. The products available on the market tend to dry out and become too hard over a period of time. The pouches are sold in boxes comprising several pouches. Once the boxes have been opened, the wetness of the pouches change over a period of 1 to 7 days. It is a challenge to provide a product in which the humidity of the environment around the opened box of pouches does not influence the quality/wetness of the product. The inventors have found that the combination of potato fibers, microcrystalline and xanthan gum at the defined ratios provide a product of which the wetness does not change significantly over time. Even when water disappears from the product, the product does not become hard but remains soft and easily wettable. Compared to known nicotine replacement products, the product of the invention remains humid even after 7 hours of exposure to air.

The filling material does not attract water to become too wet, nor does it lose water to become too dry. The combination of potato fibers, microcrystalline and xanthan gum at the defined ratios, both improves the texture and stability of the product.

Besides, the filler consists of cheap products that are readily available at low costs.

The product comprising the filler combined with the xanthan gum at the defined ratios, provides for a simple and cost-effective dosage, which allows quick initial release of nicotine and *Cannabis* followed by a controller release of the substances over a period of 1 to 3 hours.

In an aspect, nicotine is present as nicotine pure and as nicotine salicylate salt at a ratio of pure to salt of 0.20-1:1, or 0.5-1:1. In one aspect, the ratio between microcrystalline cellulose, potato fibers and xanthan gum is 1.8-4.8:1:0.001-0.39. These specific ratios further improve the wettability, palatability and release profiles of the product of the invention.

In another aspect, no nicotine is present. In yet another aspect, no *Cannabis* is present. The quality of the product, such as wettability, water retention, palatability, and the like, are not dependent on the amounts of nicotine or *Cannabis* present in the product. These amounts can be varied freely within the weight percentages mentioned. This improves the flexibility of use of the product.

The total amount of filler is preferably less than 75 wt %, or between 67 and 74 wt In a further aspect, the pH regulator is sodium bicarbonate and the sweetener is xylitol. Sodium bicarbonate and xylitol are well tolerated, relatively cheap and readily available. Sodium bicarbonate is believed to improve the wettability and thus the palatability of the product.

In yet a further aspect, the filling material comprises or consisting of
i) 0 to 5 wt % *Cannabis*,
ii) 0 to 5 wt % nicotine, whereby nicotine is either
  iib) present as nicotine pure and as nicotine salicylic acid salt at a ratio of pure to salt of 0.20-1:1, and
iii) 10 to 13 wt % of a sweetener,
iv) 6 to 20 wt % of a pH regulator,
v) 0 to 0.45 wt % of essential oil as taste agent,
vi) up to 76 wt % of a filler consisting of
  vi-1) 42 to 60 wt % microcrystalline cellulose and
  vi-2) 11 to 22 wt % potato fibers,
  whereby a ratio between microcrystalline cellulose and potato fibers is 2.0-5:1, and
vii) 0.1 to 5 wt % of xanthan gum as a wetting agent,
whereby a ratio between microcrystalline cellulose, potato fibers and xanthan gum is 1.0-5:1:0.001-0.4, wherein wt % are weight percentages of the total weight of the filling material.

In an aspect, nicotine is present as nicotine pure and as nicotine salicylate salt at a ratio of pure to salt of 0.20-1:1. In another aspect, the ratio between microcrystalline cellulose, potato fibers and xanthan gum is 3.2-4.6:1:0.1-0.38. These specific ratios further improve the wettability, humidity, palatability and release profiles of the product of the invention.

In an aspect, the filling material comprises or consisting of
i) 0.01 to 10 wt % *Cannabis*,
ii) 0 to 6 wt % nicotine, whereby nicotine is either
  iia) present in the form of tobacco or
  iib) present as nicotine pure and as nicotine salicylic acid salt at a ratio of pure to salt of 0.23-1:1, and
iii) 10 to 13 wt % of a sweetener,
iv) 6 to 20 wt % of a pH regulator,
v) 0 to 0.45 wt % of essential oil as taste agent,
vi) up to 75 wt % of a filler consisting of
  vi-1) 55 to 59 wt % microcrystalline cellulose and
  vi-2) 13 to 17% wt % potato fibers,
  whereby the ratio between microcrystalline cellulose and potato fibers is 3.5-3.9:1, and
vii) 2 to 5 wt % of xanthan gum as a wetting agent,
whereby the ratio between microcrystalline cellulose, potato fibers and xanthan gum is 3.0-5:1:0.01-0.4, wherein wt % are weight percentages of the total weight of the filling material.

In an aspect, nicotine is present as nicotine pure and as nicotine salicylate salt at a ratio of pure to salt of 0.20-1:1. In another aspect, the ratio between microcrystalline cellulose, potato fibers and xanthan gum is 3.2-4.6:1:0.1-0.38. These specific ratios further improve the wettability, humidity, palatability and release profiles of the product of the invention.

In yet another aspect, no nicotine is present. In an aspect, no nicotine is present and *Cannabis* is present as CBD at a 1 to 5 wt %.

In one aspect, the pH regulator is sodium bicarbonate and the sweetener is xylitol.

In a further aspect, the filling material comprises 0.01 to 7 wt % *Cannabis* and 0 to 6 wt % nicotine present as nicotine pure and as nicotine salicylic acid salt at a ratio of pure to salt of 0.23-1:1.

In an aspect, *Cannabis* is cannabidiol (CBD), tetrahydrocannabinol (THC), cannabinol (CBN) or any stereoisomer, diastereomer or metabolite thereof. In one aspect, *Cannabis* is wherein *Cannabis* is cannabidiol (CBD) or any stereoisomer, diastereomer or metabolite thereof, or any mixture thereof.

In another aspect, the filling material comprises or consisting of
ii) 0 to 6 wt % nicotine, whereby nicotine is
  iib) present as nicotine pure and as nicotine salicylate salt at a ratio of pure to salt of 0.20-1:1, and
iii) 9 to 13 wt % of a sweetener,
iv) 9.5 to 12 wt % of a pH regulator,
v) 0 to 0.4 wt % of essential oil as taste agent,
vi) up to 75 wt % of a filler consisting of
  vi-1) 52 to 58 wt % microcrystalline cellulose and
  vi-2) 13 to 16% wt % potato fibers,
  whereby the ratio between microcrystalline cellulose and potato fibers is 3.3-4.2:1, and
vii) 2 to 5 wt % of xanthan gum as a wetting agent,
whereby the ratio between microcrystalline cellulose, potato fibers and xanthan gum is 3.0-5:1:0.01-0.4, wherein wt % are weight percentages of the total weight of the filling material.

In an aspect, nicotine is present as nicotine pure and as nicotine salicylate salt at a ratio of pure to salt of 0.20-1:1. In another aspect, the ratio between microcrystalline cellulose, potato fibers and xanthan gum is 3.2-4.6:1:0.1-0.38. These specific ratios further improve the wettability, humidity, palatability and release profiles of the product of the invention.

In yet another aspect, no nicotine is present.

In a further aspect, the pH regulator is sodium bicarbonate and the sweetener is xylitol.

In an aspect, microcrystalline cellulose has a particle size between 70 and 500 µm, or for 50% a particle size of less than or about 149 µm. This size assures that the particles are less than the average particle size of the potato fibers and thus provides for a three dimensional network that allows proper mixing with the other ingredients in such a manner that ingredients like taste agents and nicotine are released at a preferable rate.

In one aspect, the use of a buffer agent is disclaimed. In another aspect, the use as chewing gum is disclaimed. In a further aspect, the use of a resin is disclaimed. In an aspect, the use of (tri)glycerides is disclaimed. In one aspect, the use of coatings is disclaimed.

In another aspect, the sweetener is selected from the group comprising xylitol, sorbitol, maltitol, aspartame and saccharin, or any mixtures thereof. In an aspect, the sweetener is xylitol. Xylitol is well tolerated and easily available at low cost.

In yet another aspect, the pH regulator is selected from the group comprising sodium carbonate, potassium carbonate, calcium carbonate, magnesium carbonate, sodium bicarbonate, phosphoric acid, sodium orthophosphate, potassium diphosphate, calcium diphosphate, sodium polyphosphate, potassium polyphosphate, lactic acid, malic acid, acetic acid, tartaric acid, succinic acid and ascorbic acid, or any mixtures thereof. In an aspect, the pH regulator is sodium bicarbonate. Sodium bicarbonate is easily available at low cost. Sodium bicarbonate is believed to improve the wettability and thus the palatability of the product.

Sodium bicarbonate is also believed to improve the water retention capability of the product.

In a further aspect, the essential oil is selected from the group comprising lavender, mint, tea tree oil, patchouli, melon, eucalyptus, liquorice, strawberry and spearmint, or any mixtures thereof.

In one aspect, the filling material comprises or consists of
i) 0.15 to 10 wt % *Cannabis,*
ii) 0 to 3 wt % nicotine, whereby nicotine is either
 iia) present in the form of tobacco or
 iib) present as nicotine pure and as nicotine salicylic acid salt at a ratio of pure to salt of 0.23-1:1, and
iii) 11 to 12 wt % of a sweetener, which is xylitol,
iv) 7.5 to 19 wt % of a pH regulator, which is sodium bicarbonate,
v) 0 to 0.4 wt % of essential oil as taste agent selected from the group comprising lavender, mint, tea tree oil, patchouli, melon, eucalyptus, liquorice, strawberry and spearmint,
vi) up to 75 wt % of a filler consisting of
 vi-1) 55 to 58 wt % microcrystalline cellulose and
 vi-2) 15 to 16% wt % potato fibers,
 whereby the ratio between microcrystalline cellulose and potato fibers is 3.6-3.8:1, and
vii) 3.5 to 3.9 wt % of xanthan gum as a wetting agent, whereby the ratio between microcrystalline cellulose, potato fibers and xanthan gum is 3.0-5:1:0.01-0.4, wherein wt % are weight percentages of the total weight of the filling material.

In another aspect, the filling material comprises or consists of
ii) 0 to 3 wt % nicotine, whereby nicotine is
 iib) present as nicotine pure and as nicotine salicylic acid salt at a ratio of pure to salt of 1:1, and
iii) 11 to 12 wt % of a sweetener, which is xylitol,
iv) 10.5 to 12 wt % of a pH regulator, which is sodium bicarbonate,
v) 0 to 0.4 wt % of essential oil as taste agent selected from the group comprising lavender, mint, tea tree oil, patchouli, melon, eucalyptus, liquorice, strawberry and spearmint,
vi) up to 75 wt % of a filler consisting of
 vi-1) 57 to 58 wt % microcrystalline cellulose and
 vi-2) 15 to 16% wt % potato fibers,
 whereby the ratio between microcrystalline cellulose and potato fibers is 3.4:1, and
vii) 3.5 to 3.9 wt % of xanthan gum as a wetting agent, whereby the ratio between microcrystalline cellulose, potato fibers and xanthan gum is 3.0-5:1:0.01-0.4, wherein wt % are weight percentages of the total weight of the filling material.

In a further aspect, nicotine is present as nicotine pure and as nicotine salicylic acid salt at a ratio of pure to salt of 0.6:1.

In one aspect, the ratio between microcrystalline cellulose, potato fibers and xanthan gum is 2.7-3.8:1:0.04-1.

The specific combinations of weight percentages and ratios mentioned herein provide for an optimum product having excellent palatability, wettability, minimum humidity loss, optimum release of nicotine, *Cannabis* and taste agent.

The invention also relates to the pouch product as defined anywhere herein for use in nicotine replacement therapy, or for use in treatment of tobacco addiction.

The invention also relates to the pouch product as defined anywhere herein, especially the product comprising *Cannabis*, for use in prevention and treatment of anxiety, cognition, movement, reduce seizures, insomnia, depression, improve symptoms of inflammatory bowel disease (IBD) and pain disorders.

The invention also relates to a method for preparation of the pouch product as defined anywhere herein. The method may comprise or consist of the step of
a) mixing the ingredients of the filling material in a container,
b) sealing the container for 1 to 3 days, or 2 days,
c) filling the filling material in the pouches,
d) sealing the pouches, e.g. by heat treatment, and
e) optionally, adding water to adapt the humidity of the filling material.

An advantage of the combination of ingredients is that the pouch product can be easily made at low production costs. No buffer or other additional agents are needed during production.

The humidity may be between 0 and 95 wt %, or between 0 and 75 wt %, or between 0 and 60 wt %, between 5 and 75 wt %, between 10 and 60 wt %, or between 25 and 75 wt %, or between 25 and 60 wt %.

DETAILED DESCRIPTION

Aspects of the present disclosure will be described more fully hereinafter. The product can, however, be realized in many different forms and should not be construed as being limited to the aspects set forth herein.

The terminology used herein is for the purpose of describing particular aspects of the disclosure only, and is not intended to limit the invention. As used herein, the singular forms "a", "an" and "the" are intended to include the plural forms as well, unless the context clearly indicates otherwise.

As used herein the term "pouch" is intended to mean a container typically formed by a web of a fibrous material enclosing a cavity. The pouch is adapted to hold the ingredients of the pouch product and for administration of the pouch product in the oral cavity. The pouch is thus adapted for oral use. The pouch is non-toxic and not water-soluble. The fibrous material may e.g. form a woven or non-woven web or fabric, such as cotton. The pouch may for example be sealed by bonding two corresponding pieces of web or fabric to each other along their edges to form a cavity for the one or more ingredients of the pouch product. In order to release the one or more ingredients, the pouch is made water-permeable so as to allow saliva from the oral cavity to penetrate the pouch and enter the cavity, where the saliva can come into contact with the ingredients of the pouch product. The pouch allows at least some of the ingredients of the pouch product to be released from the pouch into the oral cavity. The pouch is at least permeable for water, nicotine, *Cannabis* and taste agent.

Unless otherwise defined, all terms used herein have the same meaning as commonly understood by one of ordinary skill in the art to which this disclosure belongs.

The invention relates to a pouch product suitable for application in an oral cavity of a human comprising a sealable pouch material containing a filling material comprising or consisting of
vi) a filler consisting of
 vi-1) 52 to 58 wt % microcellulose and
 vi-2) 13 to 16% potato's fibers, whereby wt % are weight percentages of the total weight of the product and
 whereby the ratio between microcellulose and potato's fibers is between 3.3 to 4.2:1,
iii) 9 to 13 wt % of a sweetener, vii) 2 to 5 wt % of a wetting agent
iv) 9.5 to 12 wt % of a pH regulator,
ii) 0 to 3 wt % nicotine, whereby nicotine is present as nicotine base and as nicotine salicylic acid salt at a ratio of base to salt between 0.43 to 1:1,
and optionally v) 0 to 0.4 wt % of essential oil as taste agent, whereby all wt % are weight percentages of the total weight of the product.

The invention also relates to a pouch product suitable for application in an oral cavity of a human comprising a sealable pouch material containing a filling material comprising or consisting of
i) *Cannabis* in an amount of 0.01 to 10 wt %,
ii) 0 to 6 wt % nicotine, whereby nicotine is either
ii1) present in the form of tobacco or
ii2) present as nicotine pure and as nicotine salicylic acid salt at a ratio of pure to salt between 0.23 to 1:1,
vi) one or more filler up to 100 wt %, and
optionally one or more additive selected from the group comprising iii) sweetener, vii) wetting agent, iv) pH regulator and v) taste agent.

The invention relates to a pouch product suitable for application in an oral cavity of a human comprising a sealable pouch material containing a filling material comprising or consisting of
i) 0 to 10 wt % *Cannabis*,
ii) 0 to 10 wt % nicotine, whereby nicotine is either
iia) present in the form of tobacco or
iib) present as nicotine pure and as nicotine salicylic acid salt at a ratio of pure to salt of 0.20-1:1, and up to 100 wt % of one or more of iii) a sweetener, iv) a pH regulator, and optionally v) essential oil as taste agent,
The filling material further comprises or consists of
vi) up to 76 wt % of a filler consisting of
vi-1) 42 to 60 wt % microcrystalline cellulose and
vi-2) 11 to 22 wt % potato fibers,
whereby the ratio between microcrystalline cellulose and potato fibers is 2.0-5:1, and
vii) 0.1 to 5 wt % of xanthan gum as a wetting agent, whereby the ratio between microcrystalline cellulose, potato fibers and xanthan gum is 1.0-5:1:0.001-0.4, wherein wt % are weight percentages of the total weight of the filling material.

The filling material may comprise i) 0 wt %, or 0 to 10 wt %, or 0.01 to 10 wt %, or 0.01 to 7 wt, or 0.5 to 8 wt %, or 1 to 8 wt %, or 1 to 6 wt %, or 1 to 5 wt %, or 1 to 3 wt %, or 0.5 to 5 wt %, or 0.5 to 3 wt % *Cannabis*, in combination with the other ingredients within their ranges and ratios as defined anywhere herein.

*Cannabis* in the pouch product may be any type of *Cannabis* or derivative or combination thereof. *Cannabis* may be selected from the group comprising or consisting of cannabinol (CBN), tetrahydrocannabinol (THC), cannabidiol (CBD), cannabigerol (CBG), cannabigerolic acid (CBGA), tetrahydrocannabinolic acid (THCA), cannabinolic acid (CBNA), or any mixtures thereof, or any stereoisomer, diastereomer or metabolite thereof, or any mixture thereof. *Cannabis* in the pouch product may be cannabidiol (CBD) and tetrahydrocannabinol (THC), or only cannabidiol (CBD), or any stereoisomer, diastereomer or metabolite thereof, or any mixture thereof.

The filling material may comprise ii) 0 wt %, or 0 to 10 wt %, or 0 to 8 wt %, or 0 to 6 wt %, or 0.5 to 8 wt %, or 1 to 8 wt %, or 1 to 6 wt %, or 1 to 5 wt %, or 1 to 3 wt %, or 0.5 to 5 wt %, or 0.5 to 3 wt %, or 3 wt % nicotine, in combination with the other ingredients within their ranges and ratios as defined anywhere herein in combination with the other ingredients within their ranges and ratios as defined anywhere herein.

The nicotine may be present in iia) the form of tobacco, especially when the pouch product comprises *Cannabis*.

The nicotine may be present iib) as nicotine pure and as nicotine salicylic acid salt. When no *Cannabis* is present, nicotine is preferably present as pure nicotine and as nicotine salicylic acid salt. The ratio of pure to nicotine salt is important for the release profile of nicotine from the pouch after application of the pouch in the oral cavity. The ratio may be 0.20 to 1:1, or 0.23 to 1:1, or 0.4-1:1, or 0.43 to 1:1, or 0.5 to 1:1, or 0.6 to 1:1. The ratio may be 0.666:1.

The filling material may comprise 0.01 to 7 wt % *Cannabis* and 0 to 6 wt % nicotine present as nicotine pure and as nicotine salicylic acid salt at a ratio of pure to salt of 0.6-1:1, in combination with the other ingredients within their ranges and ratios as defined anywhere herein.

The filling material may comprise up to 100 wt % of one or more of iii) a sweetener, iv) a pH regulator, and optionally v) essential oil as taste agent.

The filling material may comprise iii) 9 to 15 wt %, or 10 to 13 wt %, or 11 to 12 wt % of a sweetener, in combination with the other ingredients within their ranges and ratios as defined anywhere herein. The sweetener may be selected from the group comprising or consisting of xylitol, sorbitol, maltitol, aspartame and saccharine, or mixtures thereof. The sweetener may be xylitol.

The filling material may comprise iv) 5 to 20 wt %, 6 to 20 wt %, or 7 to 19 wt %, or 7.5 to 19 wt % of a pH regulator, when the filler material comprises *Cannabis*, in combination with the other ingredients within their ranges and ratios as defined anywhere herein.

The filling material may comprise iv) 6 to 20 wt %, or 8 to 15 wt %, or 8 to 13 wt %, 9.5 to 12 wt %, or 10 to 12 wt %, or 10.5 to 12 wt %, or 11 to 12 wt % of a pH regulator, when the filler material does not comprises *Cannabis*, in combination with the other ingredients within their ranges and ratios as defined anywhere herein.

The pH regulator may be selected from the group comprising sodium carbonate, potassium carbonate, calcium carbonate, magnesium carbonate, sodium bicarbonate, phosphoric acid, sodium orthophosphate, potassium diphosphate, calcium diphosphate, sodium polyphosphate, potassium polyphosphate, lactic acid, malic acid, acetic acid, tartaric acid, succinic acid and ascorbic acid, or any mixtures thereof. The pH regulator may be a carbonate or a bicarbonate. The pH regulator may be sodium bicarbonate.

The filling material may comprise v) 0 to 0.45 wt %, or 0 to 0.4 wt %, or 0.1 to 0.45 wt %, or 0.5 to 0.35 wt %, or 0.5 to 0.3 wt % of essential oil as taste agent, in combination with the other ingredients within their ranges and ratios as defined anywhere herein.

The taste agent may be an essential oil. The taste agent may be selected from the group comprising or consisting of lavender, mint, tea tree oil, patchouli, melon, eucalyptus, liquorice, strawberry and spearmint.

The filling material further comprises a filler. The filling material may comprise vi) up to 100 wt %, or up to 75 wt %, or up to 74 wt %, or 50 to 77 wt %, or 50 to 75 wt %, or 50 to 74 wt %, or 60 to 74 wt %, or 70 to 75 wt %, or 70 to 74 wt % of a filler, in combination with the other ingredients within their ranges and ratios as defined anywhere herein.

The filler consists of a combination of microcrystalline cellulose and potato fibers at a specific ratio. The ratio may be 2.0 to 5:1, or 2.5 to 4.5:1, or 3.3 to 4.2:1, or 3.4 to 4.1:1, or 3.5-3.8:1, or 3.4:1, or 0.28 to 0.3:1, or 0.29:1, when the filler material does not comprise *Cannabis*, in combination with the other ingredients within their ranges and ratios as defined anywhere herein.

The ratio may be 2.0 to 5:1, or 2.5 to 4.5:1, or 3.3 to 4.0:1, or 3.4 to 4.0:1, or 3.5-3.9:1, or 3.6 to 3.8:1, when the filler material does comprises *Cannabis*, in combination with the other ingredients within their ranges and ratios as defined anywhere herein.

The filler may comprise vi-1) 42 to 60 wt %, or 45 to 60 wt %, or 52 to 58 wt %, or 55 to 58 wt %, or 57 to 58 wt % microcrystalline cellulose, when the filler material does not comprise *Cannabis*, in combination with the other ingredients within their ranges and ratios as defined anywhere herein.

The filler may comprise vi-1) 42 to 60 wt %, or 52 to 60 wt %, or 55 to 59 wt %, or 55 to 58 wt % microcrystalline cellulose, when the filler material does comprise *Cannabis*, in combination with the other ingredients within their ranges and ratios as defined anywhere herein.

Microcrystalline cellulose may have a particle size between 70 and 500 µm, or between 100 and 250 µm, or between 120 and 175 am. At least 50% of the microcrystalline cellulose particles may have size or diameter of less than or about 149 µm.

The filler may comprise vi-2) 11 to 22 wt %, or 13 to 17% wt %, %, or 13 to 16 wt %, or 14 to 16 wt %, or 15 to 16 wt %, of potato fibers, when the filler material does not comprise *Cannabis*, in combination with the other ingredients within their ranges and ratios as defined anywhere herein.

The filler may comprise vi-2) 11 to 22 wt %, or 10 to 20 wt %, or 13 to 17% wt %, %, or 13 to 15 wt %, or 14 to 16 wt %, or 15 to 16 wt %, of potato fibers, when the filler material does comprise *Cannabis*, in combination with the other ingredients within their ranges and ratios as defined anywhere herein.

Potato fibers may have a particle size between 250 and 5000 µm, or between 500 and 3000 µm, or between 1000 and 4000 µm. At least 50% of the potato fibers particles may have size or diameter larger than 250 µm, or 1000 µm, 1500 µm, or 2500 µm.

The filling material may comprise vii) 0.1 to 5 wt %, or 0.5 to 5 wt %, or 1 to 5 wt %, or 1 to 4 wt %, or 2.5 to 4.5 wt %, or 3 to 4 wt %, or 3.5 to 3.9 wt % of xanthan gum as a wetting agent, in combination with the other ingredients within their ranges and ratios as defined anywhere herein.

The ratio between microcrystalline cellulose, potato fibers and xanthan gum is important for the quality of the pouch product in terms of humidity, release profile of *Cannabis*, nicotine and taste agents, water retainment, palatability and the like. The ratio microcrystalline cellulose:potato fibers:xanthan gum may be 1.0-5:1:0.001-0.4, or 1.5-5:1:0.001-0.4, or 1.7-4.8:1:0.001-0.39, or 1.8-4.75:1:0.001-0.39, or 2.0-4.8:1:0.001-0.4, or 3.2-4.6:1:0.001-0.38, or 3.5-4.5:1:0.01-0.3, or 3.5-4:1:0.1-0.3, or 2.7-3.8:1:0.04-1.

Medical Use

The pouch product as defined anywhere herein may be used in nicotine replacement therapy or in treatment of tobacco addiction.

The pouch product as defined anywhere herein may be used in prevention and treatment of anxiety, cognition, movement, reduce seizures, insomnia, depression, improve symptoms of inflammatory bowel disease (IBD) and pain disorders.

The pouch product comprising *Cannabis* is believed to be especially useful in prevention and treatment of anxiety, cognition, movement, reduce seizures, insomnia, depression, improve symptoms of inflammatory bowel disease (IBD) and pain disorders.

Pain disorders includes pain caused by injuries or any other diseases. The pain disorder may be related to pain caused by inflammation, cancer, multiple sclerosis and arthritis.

Examples

The composition of example 1 (0 wt % nicotine) and example 2 (3 wt % nicotine) are outlined in table 1. The ingredients were dry mixed and then filled into a pouch or bag. The pouch was then sealed using heat.

TABLE 1

| Ingredient | g | g | % | % | 1 pouch a 0.6 g | 1 pouch a 0.6 g |
|---|---|---|---|---|---|---|
| Microcellulose (Cas nr 9004-34-6) | 15 | 15 | 57.69 | 53.38 | 0.35 | 0.32 |
| Potato fibers | 4 | 4 | 15.38 | 14.23 | 0.09 | 0.09 |
| Xylitol | 3 | 3 | 11.54 | 10.68 | 0.07 | 0.06 |
| Xanthan gum | 1 | 1 | 3.85 | 3.56 | 0.02 | 0.02 |
| NaHCO$_3$ | 3 | 3 | 11.54 | 10.68 | 0.07 | 0.06 |
| Nicotine | | | | | | |
| pure nicotine | 0 | 0.8 | 0.00 | 2.85 | 0.00 | 0.02 |
| Nicotine salt (salicylic acid) | 0 | 1.2 | 0.00 | 4.27 | 0.00 | 0.03 |
| Essential oil | 0 | 0.1 | 0.00 | 0.36 | 0.00 | 0.00 |
| Total | 26 | 28.1 | 100.00 | 100.00 | 0.60 | 0.60 |

The weight of nicotine is 3 wt % at the most or 18 mg per pouch. The nicotine is present as nicotine base (pure) and nicotine salicylic acid at a ratio of 1:1 or 0.43:1.

The composition of example 3 (0 wt % nicotine) and example 4 (3 wt % nicotine) are outlined in table 2. The ingredients were dry mixed and then filled into a pouch or bag. The pouch was then sealed using heat.

TABLE 2

| Ingredient | g | g | % | % | 1 pouch a 0.6 g | 1 pouch a 0.6 g |
|---|---|---|---|---|---|---|
| CDB | 0.04 | 1.77 | 0.16 | 5.55 | 0.00 | 0.03 |
| Microcellulose (Cas nr 9004-34-6) | 15 | 15 | 59.90 | 47.07 | 0.36 | 0.28 |
| Potato fibers | 4 | 4 | 15.97 | 12.55 | 0.10 | 0.08 |
| Xylitol | 3 | 3 | 11.98 | 9.41 | 0.07 | 0.06 |
| Xanthan gum | 1 | 1 | 3.99 | 3.14 | 0.02 | 0.02 |
| NaHCO$_3$ | 2 | 5 | 7.99 | 15.69 | 0.05 | 0.09 |
| Nicotine | | | | | | |
| Pure nicotine | 0 | 0.8 | 0.00 | 2.51 | 0.00 | 0.02 |
| Nicotine salt (salicylic acid) | 0 | 1.2 | 0.00 | 3.77 | 0.00 | 0.02 |
| Essential oil | 0 | 0.1 | 0.00 | 0.31 | 0.00 | 0.00 |
| Total | 25.04 | 31.87 | 100.00 | 100.00 | 0.60 | 0.60 |

The weight of nicotine is 3 wt % at the most or 18 mg per pouch. The nicotine is present as nicotine base (pure) and nicotine salicylic acid at a ratio of 1:1 or 0.43:1.

Release Study:

The release of nicotine and/or *Cannabis* may be measured using a dissolution test of the FDA, e.g. FDA-2018-D-2614 for "Dissolution Testing and Acceptance Criteria for Immediate-Release Solid Oral Dosage Form Drug Products Containing High Solubility Drug Substances.".

TABLE 3

| Ingredient | g | % |
| --- | --- | --- |
| Microcellulose (Cas nr 9004-34-6) | 22 | 34.15 |
| potato fibers | 8 | 12.42 |
| Xylitol | 14 | 21.73 |
| xanthan gum | 0.42 | 0.65 |
| NaHCO$_3$ | 8 | 12.42 |
| Nicotine | | |
| pure nicotine | 3 | 4.66 |
| Nicotine salt (salicylic acid) | 5 | 7.76 |
| Essential oil | 4 | 6.21 |
| Total | 64.42 | 100.00 |

Samples with the same matrix (table 3) were prepared with the same amount of nicotine. The ratio of pure nicotine and nicotine salicylate were varied.

The samples were prepared in 350 mg (±20 mg) pouches and extracted in 100 ml pQ water through continuous flow in an extraction tube pumped at the rate of 3 ml/s.

Analysis of the released nicotine was done with a UV-Vis Spectrometer at 290 nm

Results

Each test was done with 2 samples of each compositions, the presented results are the average of both data points. Increasing the pure nicotine content flattened the release curve.

TABLE 4

Results for a sample with a ratio of 1:3 Pure Nicotine to Nicotine Salicylate.

| time (min) | 5 | 15 | 25 | 60 |
| --- | --- | --- | --- | --- |
| Absorption | 1.88 | 2.4 | 2.432 | 2.592 |
| Concentration (g/L) | 0.02638 | 0.06087 | 0.06168 | 0.06573 |
| Release (%) | 40.13 | 92.59 | 93.83 | 99.4 |

TABLE 5

Comparison of the release rate of nicotine for different ratios of pure Nicotine and Nicotine Salicylate.

| Ratio (Pure Nic. To Nicotine Salicylate) | 5 min | 15 min | 25 min | 60 min |
| --- | --- | --- | --- | --- |
| 1:0 | 35.14 | 74.27 | 75.86 | 85.23 |
| 1:1 | 37.46 | 89.03 | 90.35 | 97.41 |
| 1:3 | 40.13 | 92.59 | 93.83 | 99.4 |
| 1:5 | 43.56 | 93.68 | 95.15 | 99.49 |
| 0:1 | 48.31 | 97.26 | 99.1 | 99.65 |

The results are expected to show that at the most 55 wt % of and/or *Cannabis* is released from the pouch within 30 second and the remaining nicotine and/or *Cannabis* is released from the pouch within following 1 to 3, or 11.5 hour.

Humidity Retention:

Samples with the same matrix and nicotine content where prepared, where the amount of xanthan gum was varied from 0 to 30 w %.

The samples were prepared in 350 mg (±20 mg) pouches and 100 mg of water was added to each pouch. The samples were then sealed for 2 days, for homogenization through diffusion.

After 2 days the samples were weighed, exposed to air in an indoor environment for 7 hours, at the same temperature (about 21° C.) and humidity (40%) and weighed after exposure to measure the weight loss.

Results

Each test was done with 2 samples of each composition, the presented results are the average of both data points.

TABLE 6

Comparison of the total weight loss in ambient air depending on the xanthan gum content.

| xanthan gum content (w %) | Mass loss (%) |
| --- | --- |
| 0 | 12.01 |
| 0.7 | 2.24 |
| 7 | 13.56 |
| 14 | 23.45 |
| Another brand 1 | 12.48 |
| Another brand 2 | 34.19 |

Results

It is interesting to observe that the addition of small amount of xanthan gum drastically lowers the weight loss but at higher concentrations the opposite effect is produced. It appears that there is an optimal amount of xanthan gum for an optimum water retention of the product.

Texture:

Samples were prepared varying the ratios of microcrystalline cellulose to potato fibers and xanthan gum.

The samples were prepared in 350 mg (±20 mg) pouches and 100 mg of water was added to each pouch. The samples were then sealed for 2 days, for homogenization through diffusion.

The samples were then left placed in a standard chewing tobacco container and opened 3 times a day for 10 days. The samples were examined for grain dispersion, humidity and retention of the aromas.

Results

It was observed that a xanthan gum content of 0.7 wt %, the qualities of the product, such as grain dispersion, humidity and retention of the aromas remained the same during the experiment. With increasing amounts of xanthan gum the texture of the product became more monolithic and gummy-like.

A pure microcrystalline cellulose matrix gave a very rigid result with no trace of humidity and very little perfume being released. Wetting resulted in the aromas being released quickly but the monolithic character of the sample remained.

A pure potato fiber matrix resulted in a grainy product. The wetness of the sample was reduced. The grain dispersion of the sample allowed for the product to be utilized as intended even though most of the taste and aromas were released quickly.

At 29 wt % of potato fibers to microcrystalline cellulose ratio, the samples were practically unaffected by the procedure. The texture remained pliable, and the aromas were at a comparable level as the starting product.

The present invention is not limited to the embodiments disclosed but may be varied and modified within the scope of the following claims.

The invention claimed is:

1. A pouch product suitable for application in an oral cavity of a human comprising a sealable pouch material containing a filling material comprising:
   0 to 10 wt % *cannabis*,
   0 to 10 wt % nicotine, whereby nicotine is
      present in the form of tobacco or
      present as nicotine pure and as nicotine salicylic acid salt at a ratio of pure to salt of 0.20-1:1, and up to 100 wt % of one or more of a sweetener, a pH regulator,
up to 76 wt % of a filler consisting of
  42 to 60 wt % microcrystalline cellulose and
  11 to 22 wt % potato fibers,
  whereby a ratio between microcrystalline cellulose and potato fibers is 2.0-5:1, and
0.1 to 5 wt % of xanthan gum as a wetting agent,
  whereby a ratio between microcrystalline cellulose, potato fibers and xanthan gum is 2.0-4.8:1:0.001-0.4, wherein wt % are weight percentages of the total weight of the filling material.

2. The pouch product according to claim 1, wherein the filling material comprises
  0.01 to 10 wt % *cannabis*,
  0 to 6 wt % nicotine, whereby nicotine is
    present in the form of tobacco or
    present as nicotine pure and as nicotine salicylic acid salt at a ratio of pure to salt of 0.23-1:1, and
  10 to 13 wt % of a sweetener,
  6 to 20 wt % of a pH regulator,
  0 to 0.45 wt % of essential oil as taste agent,
  up to 75 wt % of a filler consisting of
    55 to 59 wt % microcrystalline cellulose and
    13 to 17 wt % potato fibers,
    whereby the ratio between microcrystalline cellulose and potato fibers is 3.5-3.9:1, and
  2 to 5 wt % of xanthan gum as a wetting agent,
    whereby the ratio between microcrystalline cellulose, potato fibers and xanthan gum is 3.5-4.5:1:0.01-0.3, wherein wt % are weight percentages of the total weight of the filling material.

3. The pouch product according to claim 2, wherein the filling material comprises 0.01 to 7 wt % *cannabis* and 0 to 6 wt % nicotine present as nicotine pure and as nicotine salicylic acid salt at a ratio of pure to salt of 0.23-1:1.

4. The pouch product according to claim 1, wherein the filling material comprises 0.01 to 7 wt % *cannabis* and 0 to 6 wt % nicotine present as nicotine pure and as nicotine salicylic acid salt at a ratio of pure to salt of 0.23-1:1.

5. The pouch product according to claim 1, wherein *cannabis* is cannabidiol (CBD), tetrahydrocannabinol (THC), cannabinol (CBN) or any stereoisomer, diastereomer or metabolite thereof.

6. The pouch product according to claim 1, wherein *cannabis* is wherein *cannabis* is cannabidiol (CBD) or any stereoisomer, diastereomer or metabolite thereof, or any mixture thereof.

7. The pouch product according to claim 1, wherein the filling material comprises
  0 to 6 wt % nicotine, whereby nicotine is
    present as nicotine pure and as nicotine salicylic acid salt at a ratio of pure to salt of 0.20-1:1, and
  9 to 13 wt % of a sweetener,
  9.5 to 12 wt % of a pH regulator,
  0 to 0.4 wt % of essential oil as taste agent,
  up to 75 wt % of a filler consisting of
    52 to 58 wt % microcrystalline cellulose and
    13 to 16 wt %-potato fibers,
    whereby the ratio between microcrystalline cellulose and potato fibers is 3.3-4.2:1, and
  2 to 5 wt % of xanthan gum as a wetting agent,
    whereby the ratio between microcrystalline cellulose, potato fibers and xanthan gum is 3.5-4.5:1:0.01-0.3, wherein wt % are weight percentages of the total weight of the filling material.

8. The pouch product according to claim 1 wherein microcrystalline cellulose has a particle size between 70 and 500 µm, or for 50% a particle size of less than or about 149 µm.

9. The pouch product according to claim 1, wherein the sweetener is selected from the group comprising xylitol, sorbitol, maltitol, aspartame and saccharin, or any mixtures thereof.

10. The pouch product according to claim 1, wherein the pH regulator is selected from the group comprising sodium carbonate, potassium carbonate, calcium carbonate, magnesium carbonate, sodium bicarbonate, phosphoric acid, sodium orthophosphate, potassium diphosphate, calcium diphosphate, sodium polyphosphate, potassium polyphosphate, lactic acid, malic acid, acetic acid, tartaric acid, succinic acid and ascorbic acid, or any mixtures thereof.

11. The pouch product according to claim 1, wherein the essential oil is selected from the group comprising lavender, mint, tea tree oil, patchouli, melon, eucalyptus, liquorice, strawberry and spearmint, or any mixtures thereof.

12. The pouch product according to claim 1, wherein the filling material comprises
  0.15 to 10 wt % *cannabis*,
  0 to 3 wt % nicotine, whereby nicotine is
    present in the form of tobacco or
    present as nicotine pure and as nicotine salicylic acid salt at a ratio of pure to salt of 0.23-1:1, and
  11 to 12 wt % of a sweetener, which is xylitol,
  7.5 to 19 wt % of a pH regulator, which is sodium bicarbonate,
  0 to 0.4 wt % of essential oil as taste agent selected from the group comprising lavender, mint, tea tree oil, patchouli, melon, eucalyptus, liquorice, strawberry and spearmint,
  up to 75 wt % of a filler consisting of
    55 to 58 wt % microcrystalline cellulose and
    15 to 16 wt %-potato fibers,
    whereby the ratio between microcrystalline cellulose and potato fibers is 3.5-3.8:1, and
  5 to 3.9 wt % of xanthan gum as a wetting agent,
    whereby the ratio between microcrystalline cellulose, potato fibers and xanthan gum is 3.5-4:1:0.1-0.3, wherein wt % are weight percentages of the total weight of the filling material.

13. The pouch product according to claim 1, wherein the filling material comprises
  0 to 3 wt % nicotine, whereby nicotine is
  present as nicotine pure and as nicotine salicylic acid salt at a ratio of pure to salt of 1:1, and
  11 to 12 wt % of a sweetener, which is xylitol,
  10.5 to 12 wt % of a pH regulator, which is sodium bicarbonate,
  0 to 0.4 wt % of essential oil as taste agent selected from the group comprising lavender, mint, tea tree oil, patchouli, melon, eucalyptus, liquorice, strawberry and spearmint,
  up to 75 wt % of a filler consisting of
    57 to 58 wt % microcrystalline cellulose and
    15 to 16% wt potato fibers,
    whereby the ratio between microcrystalline cellulose and potato fibers is 3.4:1, and
  3.5 to 3.9 wt % of xanthan gum as a wetting agent,
    whereby the ratio between microcrystalline cellulose, potato fibers and xanthan gum is 3.5-4:1:0.1-0.3, wherein wt % are weight percentages of the total weight of the filling material.

14. The pouch product according to claim 1, wherein nicotine is present as nicotine pure and as nicotine salicylic acid salt at a ratio of pure to salt of 0.6:1.

15. The pouch product according to claim 1 for use in nicotine replacement therapy, or for use in treatment of tobacco addiction.

16. The pouch product according to claim 1 for use in prevention and treatment of anxiety, cognition, movement, reduce seizures, insomnia, depression, improve symptoms of inflammatory bowel disease (IBD) and pain disorders.

* * * * *